United States Patent [19]

Yasumoto

[11] 4,005,721
[45] Feb. 1, 1977

[54] DENTAL FLOSS HOLDER

[76] Inventor: Michio Yasumoto, 3909 NE. 135th St., Portland, Oreg. 97230

[22] Filed: Mar. 17, 1975

[21] Appl. No.: 558,804

[52] U.S. Cl. .................................... 132/91
[51] Int. Cl.² .................................... A61C 15/00
[58] Field of Search .................. 132/91, 92, 89

[56] References Cited

UNITED STATES PATENTS

| | | | |
|---|---|---|---|
| 691,581 | 1/1902 | Baumeister | 132/91 |
| 1,161,043 | 11/1915 | Gallas | 132/92 A |
| 1,306,998 | 6/1919 | Dimitroff | 132/92 A |
| 1,553,818 | 9/1925 | Hope | 132/92 R |
| 2,784,722 | 3/1957 | Chamberlin et al. | 132/92 R |
| 3,759,272 | 9/1973 | Vincenti | 132/92 R |
| 3,886,956 | 6/1975 | Cash | 132/91 |

*Primary Examiner*—G.E. McNeill
*Attorney, Agent, or Firm*—Chernoff & Vilhauer

[57] ABSTRACT

A dental floss holder particularly suited for access to all teeth in the user's mouth and rapid replacement of dental floss. A hollow handle is adapted to hold a source spool of dental floss interior thereto and to receive a plurality of interchangeable bifurcated tips for holding a taut piece of floss at different respective orientations relative to the handle for convenient access to all teeth in the user's mouth. A pivotally mounted tip is also provided for adjustable placement in several convenient orientations. The source end of the dental floss is fixedly grasped by a quickly-operated lock mechanism connected to a shaft interior to the handle which both rotatably supports the spool of floss and transmits rotational or longitudinal motion from an actuator at one end of the handle to the lock mechanism for releasing a fresh piece of dental floss. The free end of the dental floss is securely held and the soiled floss is cut off by a fastener disposed at an extremity of one branch of each tip, which avoids contamination of the holder or fresh, unused floss.

13 Claims, 10 Drawing Figures

DENTAL FLOSS HOLDER

BACKGROUND OF THE INVENTION

This invention relates to dental floss holders for facilitating the cleaning of teeth.

In the use of dental floss to clean one's own teeth it is often difficult to position and manipulate the floss for proper use. The floss must be stretched tightly, and the required force tends to cause the floss to slip off of or cut into the user's fingers. Also the user's hand is frequently too large to be comfortably inserted in his mouth sufficiently to place floss between the teeth farthest back in his mouth; in fact, the user ordinarily needs to use both hands to manipulate the dental floss anyway. In addition, when cleaning an entire set of teeth it usually becomes necessary to use several pieces of new dental floss as the floss becomes soiled. Thus even though the user may be able to find a comfortable way of holding one piece of dental floss that piece must be discarded and the user must find a comfortable way of holding a new piece of floss.

Mechanical dental floss holders have previously been designed for facilitating the cleaning of one's own teeth with a taut length of dental floss. For example, Kristmann U.S. Pat. No. 1,274,423 discloses a dental floss case which includes a chamber for holding a roll of dental floss and a forked end having a pair of prongs across which a length of dental floss is stretched. A principal drawback of the Kristmann device is that the shape of the forked end is not convenient for reaching all teeth within the user's mouth since the body of the device would have to be placed vertically adjacent the user's face in order to place the floss in gaps between the upper and lower front teeth. Another drawback is that the floss is threaded from inside the body of the device across the space between the aforementioned prongs, back inside the body of the device and out an opening near the source roll of dental floss. Consequently soiled floss will move through the body of the device as the floss is used up and may shed some of its waste material within the body of the device leading to unsanitary conditions which would tend to contaminate the unused floss and render the device unfit for placement within one's mouth without frequent cleaning. Also, since both the supply and free ends of the floss appear to be secured by the same locking mechanism it may be difficult to stretch the length of dental floss tightly between the two prongs of the forked end; in any case, the floss must be released by the time-consuming process unscrewing a knob.

Other dental floss holders, such as the devices disclosed in Casselman U.S. Pat. No. 3,746,017 and Henerlau U.S. Pat. No. 1,417,518, utilize tips having a gap facing to the side of holder handle, across which a length of dental floss is stretched. While dental floss holders having such tips may be more convenient for reaching some teeth than the forked end disclosed in the above-cited Kristmann device, they are unsatisfactory for reaching others.

Therefore it can be seen that there is a need for a dental floss holder which provides convenient access with a taut piece of floss to all teeth in the user's mouth and is capable of holding a sanitary supply of dental floss interior thereto for continuously replenishing the floss while minimizing contamination of the mouth from waste material previously collected on the floss. Furthermore the floss holder should be provided with a quickly-operated, easily-workable lock mechanism which grasps the fresh dental floss at its source for tightly stretching the dental floss when replacing soiled floss with new, clean material.

SUMMARY OF THE INVENTION

The present invention is directed to a new and useful dental floss holder which overcomes the drawbacks of prior art dental floss holders and meets the aforementioned needs by utilizing interchangeable tips of differing orientation for supporting a taut length of dental floss at the end of an elongate handle adapted for carrying a supply of dental floss therein.

Each of the tips comprises a bifurcated member which holds a length of dental floss stretched between the branches thereof. The bifurcated member is attached by a threaded cylindrical mounting member to the handle of the dental floss holder at the bottom or a side extremely of the bifurcated member depending upon whether the gap between the branches is to be oriented forwardly or toward the side of the handle. Dental floss is threaded from within the body of the holder through the mounting shaft of the attached tip and across the gap between the extremeties thereof. The tip which mounts with its gap toward the side of the handle provides particularly good access to the front teeth while the tip which mounts with its gap oriented forwardly provides ready access to teeth further back in the mouth. In addition, a tip may be provided with a bifurcated member whose position is adjustable.

Each tip is provided with a channel or hole at the extremity of one branch through which the floss is threaded and a fastener at the other branch extremity for securing the loose end of the dental floss and cutting the soiled dental floss from the fresh supply. Utilization of a fastener and cutting device at one extremity of the tip ensure that the waste material collected on soiled dental floss will not be exposed to unused dental floss or shed interior to the holder. Furthermore, this arrangement provides a convenient means for tightly stretching the dental floss across the gap between extremities of the tip.

Either of two locking mechanisms are provided for grasping the source end of the dental floss interior to the handle of the dental floss holder so that the floss may be stretched tightly across the tip. Both locking mechanisms utilize a shaft disposed interior to the body of the dental floss holder longitudinally relative thereto for both rotatably mounting a spool of fresh dental floss and for transmitting motion form an actuation member to a grasping mechanism.

One of the locking mechanisms utilizes an end piece, attached to the end of the handle opposite the tip end, having a push-button mounted therein which transmits compressive force to the aforementioned shaft. Dental floss is threaded off the spool through a hole to the interior of the shaft and out the tip end of the shaft which has a plurality of pinching members which ordinarily grasp the dental floss threaded there-through under spring force, but release the dental floss when the push-button is actuated thereby releasing the spring force. The floss is threaded from the pinching members through the mounting member of the tip and across the extremities thereof. This locking mechanism provides a means for rapidly releasing fresh dental floss so that it may be easily pulled off the rotatably-mounted spool, yet provides a strong grasp for tightly stretching the dental floss across the tip.

A second locking mechanism utilizes a tubular-shaped handle and a pair of plates disposed transversely interior thereto, one of the plates being fixedly mounted to the aforementioned shaft and the other plate being rotatably mounted to the center of the shaft in front of the first plate, each plate having an edge lobe portion which rubs against the interior surface of the handle to resist rotation thereof and an edge portion spaced from the interior surface to permit dental floss to be threaded there-between. The dental floss is threaded off of the spool between the lobes of the plates so that when the shaft is rotated the floss will be either pinched between the lobes or released, depending upon the direction which the shaft is rotated, since the rotatably mounted plate tends not to turn due to the friction thereof against the inside surface of the handle. The shaft is removably attached to an end piece which snaps into the end of the body opposite the tip for rotation therein to transmit rotational motion down the shaft to the plates. This locking mechanism is particularly suited for quick replacement of the dental floss while providing a means for securely grasping the floss to stretch it across the tip.

It is therefore a principal objective of the present invention to provide a new and improved dental floss holder for facilitating the cleaning of teeth.

It is a further principal objective of the present invention to provide such a dental floss holder which may be used conveniently to reach all teeth in the user's mouth.

It is a further objective of the present invention to provide such a dental floss holder which minimizes the possibility of contamination of the user's mouth from waste material collected on used dental floss.

It is yet another objective of the present invention to provide an easily workable mechanism for tightly grasping and releasing a length of dental floss at its source for tightly stretching the dental floss when replacing soiled floss with new, clean material.

It is a principal feature of the present invention that it utilizes interchangeable bifurcated tips of different orientation across which dental floss is tightly stretched for reaching all portions of the user's mouth.

It is another feature of the present invention that it utilizes fastening and cutting means disposed at the extremity of a branch of each tip.

It is a further feature of the present invention that it utilizes a shaft disposed within the body of the holder longitudinally relative thereto which serves the dual purpose of supporting a rotatably mounted spool of fresh dental floss while transmitting force from an end piece to a grasping mechanism for tightly locking the source end of dental floss stretched across the tip of the holder.

The foregoing and other objectives, features and advantages of the present invention will be more readily understood upon consideration of the following detailed description of the invention taken in conjunction with the accompanying drawings.

DETAILED DESCRIPTION OF THE INVENTION

Figure 1:
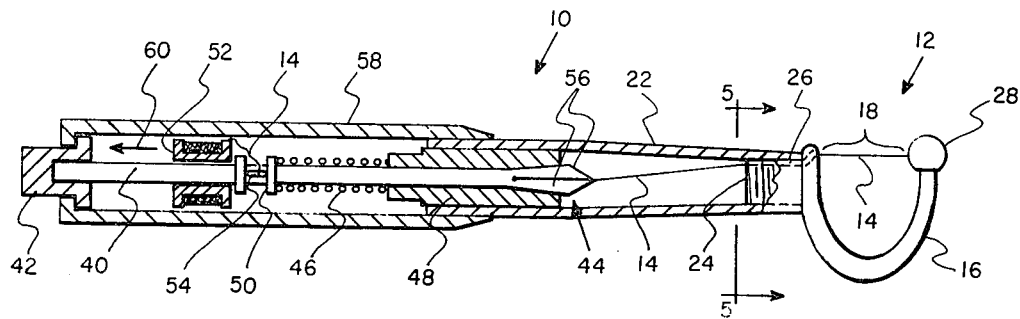
FIG. 1 is a side, partially sectional view of a preferred embodiment of the dental floss holder of the present invention, including a sideways-facing removable bifurcated tip.
Figure 2:
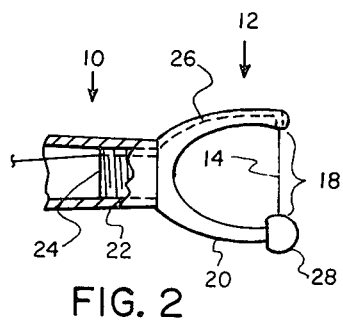
FIG. 2 is a side view of an alternative forwardly-facing tip.

Referring to FIG. 1, each embodiment of the dental floss holder includes an elongate handle 10 to which a bifurcated tip 12 is attached at one end for supporting a taut length of dental floss 14. The tip 12 may be of either the side-mounting type 16, wherein the gap 18 across which the length of floss 14 is stretched faces to the side of the handle 10 as shown in FIG. 1, or of the bottom-mounting type 20, wherein the gap 18 opens to the front of the handle 10 as shown in FIG. 2. In any case the tip 12 is releasably mounted to a body portion 22 of the handle 10 by a mounting member 24 inserted in the front end of the body 22.

The side-mounting tip 16 and the bottom-mounting tip 20 each provide distinct advantages in reaching certain areas of one's mouth while cleaning one's teeth with dental floss. That is, the side-mounting tip is particularly suitable for cleaning between front teeth while the bottom-mounting tip is more suitable for cleaning between back teeth. Therefore each dental floss holder is preferably provided with both a side-mounting tip 16 and a bottom-mounting tip 20 which are interchangeable with one another. To provide for interchangeability and to ensure that the tip may be securely fastened to the body 22 the mounting member 24 of each tip is preferably cylindrical in shape with exterior threads which mate with interior threads in a circular opening in the front end of the body member 22. However, it is recognized that other tip fastening mechanisms might be utilized without departing from the principles of this invention.

Figure 3A:
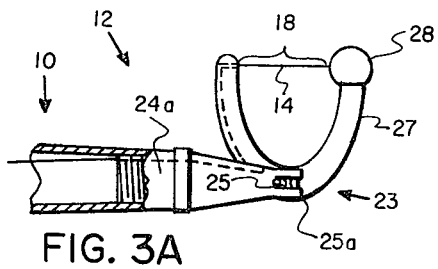
FIG. 3A is a side view of an alternative tip having a pivotally mounted bifurcated portion.
Figure 3B:
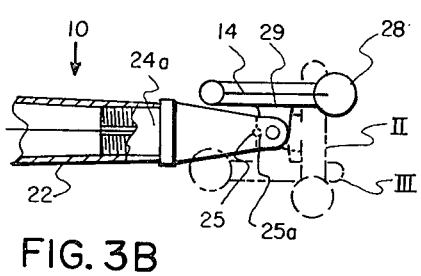
FIG. 3B is a side view of the tip of FIG. 3A rotated 90°, showing two moved positions of the bifurcated portion.

In FIGS. 3A—3B an alternative tip 27 is shown wherein the bifurcated portion may be moved into any of several positions. The tip is provided with a mounting member 24a which has a forked end 23 and a detent 25 disposed between the tines of the forked end. The bifurcated portion of the tip 27 includes a tab 29 attached to the bottom thereof, having several indentations 25a for receiving the detent 25 and being pivotally mounted between the tines of the mounting member 24a such that the gap 18 of the tip always faces to the side of the handle 10 but the length of floss 14 stretched thereacross may be positioned at various angles to the axis of the handle, depending upon the positions of the indentations 25a. Preferably, three indentations should be provided so that the floss is either locked parallel to and on either side of the handle for easy access to front teeth, as shown by positions I and III of FIG. 3B, or perpendicular to the handle for easy access to rear teeth, as shown by position II. Also, the bifurcated portion could be pivotally connected to the mounting member so that the gap 18 would be locked either into a sideways or forward orientation similar to tips 16 and 20, respectively.

Figures 4A, 4B, 5:
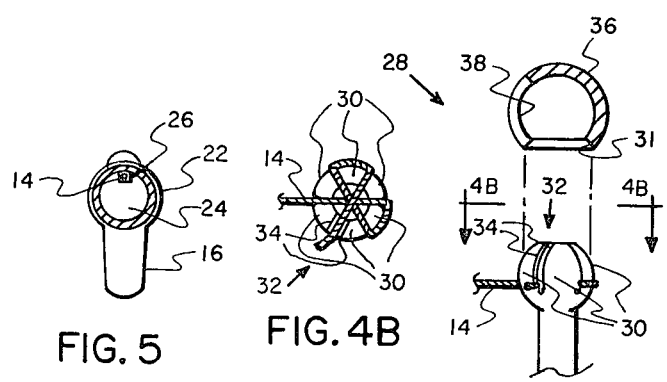
FIG. 4A is a side, exploded view of a fastener attached to an extremity of each of the tips.
FIG. 4B is a top view of the fastener of FIG. 4A with its cap removed.
FIG. 5 is a sectional view of the dental floss holder taken along line 5—5 of FIG. 1.

The dental floss 16 is threaded from a source of fresh, clean floss within the handle 10 through a passageway 26, preferably a channel as shown in FIG. 5, to the exterior of the handle 10 and from the extremity of one branch of the tip across the gap 18 to the extremity of the other branch where it is attached by a fastener 28. The use of a channel as a passageway is advantageous in that it expedites threading of the tips when they are changed by eliminating the difficulty that would be encountered in pushing the floss through a tunnel-type aperture. A locking mechanism is provided interior to the handle 10 for grasping the floss so that it may be stretched tightly across the gap 18 without any significant difficulty. In the case of the bottom-mounting tip the passageway 26 must extend along one branch to its extremity as shown in FIG. 2.

Referring to FIGS. 4A and 4B the fastener 28 utilizes a plurality of outwardly projecting fingers 30 in the shape of sections of a generally spherical knob disposed at the fastener extremity of the tip. The floss 14 is wound through spaces between the fingers, around some of the finger and through a cutting space 32 having a pair of sharp edges 34, in contrast to the other spaces between the fingers 30. Thereafter, a generally spherically-shaped cap 36, having an opening 31 for receiving the fingers 30 and slot 38 perpendicular to the opening, is snapped over the fingers with the slot straddling the dental floss 14 where it enters the fastener. When the cap 36 is snapped over the fingers the spaces there-between close, thereby securing the floss in all but the cutting space 32 where the floss is severed by the sharp edges 34. This fastener arrangement placed at one extremity of the tip eliminates the need for leaving any soiled dental floss attached to the dental floss holder when a new length is drawn between the gap 18, while preventing waste of fresh dental floss. Although a generally spherical fastener has been shown here it is recognized that other shapes could be used as long as they provide adequate resistance against the cap's releasing interior to the mouth.

Turning to the mechanism for fixedly locking the source of fresh dental floss, the preferred embodiment shown in FIG. 1 utilizes an elongate shaft 40 disposed interior to the handle 10, longitudinally relative thereto, releasably engaging a push-button 42 at the rear of the handle, having a clasp 44 integrally disposed at its front end, and being rearwardly biased by a spring 46 which acts against a stop member 50 and a sleeve 48 through which the shaft 40 is slideably inserted. A spool of floss 52 is rotatably mounted on the shaft 40 and the floss 14 is threaded through a hole 54 in the shaft and out the front end of the shaft between pinching members 56 of the clasp 44. The entire locking mechanism is held together by an end piece 58 which is threaded on or otherwise releasably attached to the body 22 for ready access to the spool of floss for replacement.

Ordinarily the shaft 40 is forced rearwardly by the spring 46 as shown by arrow 60, thereby forcing the clasp 44 into the sleeve 48 which forces the pinching members 56 together causing them to tightly grasp the floss 14. However, when the push-button 42 is pressed the spring 46 is compressed and the shaft moves in the opposite direction through the sleeve thereby pushing the pinching members outside the insert and permitting them to expand outwardly under inherent spring force to release the dental floss 14 so that more fresh dental floss may be pulled off of the spool 52 through the shaft, out the body and across the gap 18. Thus, the shaft facilitates the efficient use of space by serving the dual functions of transmitting motion to the locking mechanism while providing support for the spool of floss. This mechanism is particularly advantageous in that soiled dental floss may be quickly replaced by removing the cap 36, which releases the free end of the dental floss, pressing the push-button 42, pulling on the floss to produce a clean portion, releasing the push button, stretching the dental floss across the gap 18 and attaching it to the fastener 28, whereby the soiled dental floss is automatically cut off and may be discarded.

Figure 6:
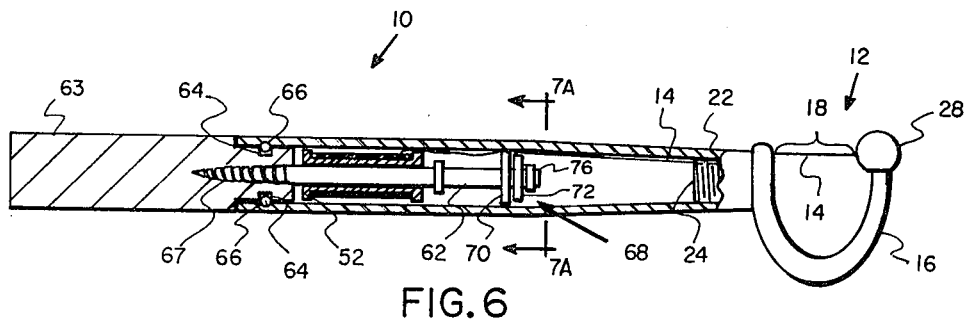
FIG. 6 is a side, partially sectional view of an alternative embodiment of the dental floss holder of the present invention, including a sideways-facing removable tip.

Turning now to an alternative embodiment of the locking mechanism as shown in FIG. 6, the locking mechanism therein also utilizes an elongate shaft disposed interior to the handle 10 of the dental floss holder. However, in this case the shaft 62 is removably, but fixedly attached at its rear end to an end piece 63 which snaps into the body 22 such that it may be rotated in order to turn the shaft and may be quickly removed for access to the interior of the body. The snap-in mounting of the end piece 63 is provided by a plurality of ball and spring or other appropriate detents 64, which fit within a groove 66 formed around the interior periphery of the rear end of the body 22. As with the preferred embodiment a spool of floss 52 is rotatably mounted upon the shaft 62, and the spool may be replaced by removing the shaft 62 from the end piece 63, as provided for example by a threaded connection 67.

Figures 7A, 7B:
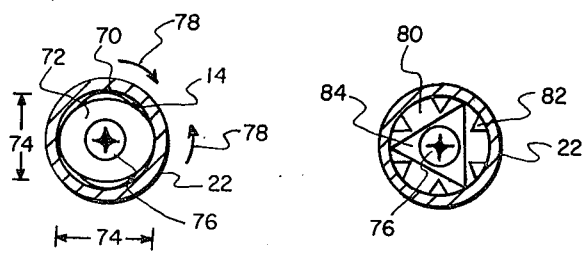
FIG. 7A is a sectional view of the dental floss holder taken along line 7A—7A of FIG. 6, showing one embodiment of a double plate-type locking mechanism.
FIG. 7B is an illustrative sectional view taken along line 7A—7A of FIG. 6 showing an alternative double plate-type locking mechanism.

A clasp mechanism 68 is mounted at the front end of the shaft. Referring to FIG. 7A as well as FIG. 6 the clasp mechanism 68 utilizes two oblong plates one of which 70 is fixedly attached perpendicular to the front end of the shaft 62, and the other of which 72 is rotatably mounted perpendicular to the center of the shaft forward of the fixedly mounted plate 70. The interior cross-section of the body 22 should be round and the dimensions of the plate are such that their greatest width 74 is equal to the interior diameter of the body so that they rub against the interior surface thereof producing friction which tends to resist their rotation. The movable plate 72 is pivotally attached by a bolt 76. The floss 14 is threaded off of the spool, between two respective lobes of the plates 70 and 72 to the floss holder tip. When end piece 63 is rotated a few degrees in one direction the lobes will move towards one another as shown by the arrows 78 since the rotation of the end piece 63 forces the plate 70 to turn while the friction against the interior wall prevents the plate 72 from turning. When the lobes come together the floss 14 is pinched there-between and locked against pulling from the free end. Naturally, the plates should not be made with sharp edges and should be provided with some relative movement in a longitudinal direction so that the floss will not be cut when their lobes approach one another. The utilization of a rotatably mounted plate 72 which is free to move relative to the body 22 further protects the floss from being cut when too much torque is applied to the end piece 63. To release the floss the handle end piece 63 is merely rotated a few degrees the opposite direction, which separates the lobes. This mechanism is particularly advantageous in that the interior mechanism may be entirely removed quickly to replace the dental floss spool and the new floss is easily threaded out to the tip.

Alternatively the plates could be made in a configuration shown in FIG. 7B where the round plate 80 is fixedly mounted perpendicular to the shaft 62 and has a plurality of notches 82 distributed around its periphery. A rotatably mounted plate 84 is provided in the shape of an equilateral triangle whose corners rub against the interior surface of the body 22. This mechanism operates in a similar manner to the two oblong plates in that the dental floss 14 is threaded through one of the notches to the top so that as the end piece 63 is rotated the notched plate 80 turns and the triangular plate 84 tends to remain stationary. This eventually causes the floss 14 to be pinched between the notched plate and a corner of the triangular plate.

The holder may be made of an inexpensive material such as plastic, although longer wear can be achieved by manufacturing the locking parts from metal or some other durable substance such as nylon. Preferably the tips should be made primarily of a somewhat soft material which would protect one's mouth from injury during use.

The terms and expressions which have been employed in the foregoing abstract and specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:
1. A dental floss holder comprising, in combination:
   a. an elongate, partially hollow body adapted to hold a supply of dental floss interior thereto;
   b. bifurcated tip means attached to a front end of said body for holding a tightly stretched length of said dental floss across a gap between two portions thereof;
   c. an elongate shaft disposed interior to said body longitudinally relative thereto;
   d. releasable clasp means disposed interior to said body and attached to the front end of said shaft for fixedly grasping a portion of dental floss; and
   e. an end piece removably attached to the rear end of said body and to said shaft, said end piece including actuation means for causing said clasp means to release its grasp by transmitting motion through said shaft.

2. The dental floss holder of claim 1 wherein said clasp means comprises a plurality of longitudinally projecting, outwardly biased pinching members attached to the front end of said shaft, a sleeve having a aperture through which said shaft is inserted such that said shaft may move back and forth longitudinally therein, and a spring connected between said shaft and said sleeve to force said shaft rearwardly enough that said pinching members are wedged into said sleeve thereby forcing said pinching members together, said pinching members being collectively larger than said aperture when they are forced together, and wherein said actuation means comprises a push-button for pushing said shaft forwardly thereby permitting said pinching members to expand outwardly and release said floss.

3. The dental floss holder of claim 1 wherein said clasp means comprises a pair of substantially parallel plates a first one of which is fixedly mounted to the front end of said elongate shaft and the second one of which is rotatably mounted to the front end of said shaft in front of said first plate, each said plate contacting the inner surface of said body at one point along its edge such that friction at said point of contact tends to resist rotation of said plates about the axis of said shaft and each said plate having a point along its edge being a predetermined distance from the interior surface of said body for threading a portion of dental floss therebetween, said end piece comprising a handle attached to the rear end of said shaft and rotatably attached to said body for axially rotating said shaft to turn said first plate.

4. The dental floss holder of claim 3 wherein the interior cross-section of said hollow body is round and said plates are oblong in shape, their greatest width being equal to the interior diameter of said body.

5. The dental floss holder of claim 3 further including a spool adapted to hold dental floss wound thereon rotatably mounted on said shaft.

6. A dental floss holder comprising, in combination:
   a. an elongate, partially hollow handle adapted to hold a supply of dental floss interior thereto;
   b. lock means disposed interior to said handle for fixedly grasping a portion of dental floss;
   c. a tip attached to one end of said handle, said tip having a bifurcated portion and a passageway formed in said tip for threading said dental floss out from the interior of said handle to the extremity of a first branch of said bifurcated portion; and
   d. fastener means disposed at the extremity of the second branch of said bifurcated portion for securing a free end of a portion of dental floss grasped by said lock means and stretched tightly between said two branches of said bifurcated portion, said fastener means comprising a plurality of adjacent fingers projecting outwardly from said second branch of said bifurcated portion toward the direction of extension of said second branch, and a cap for placement over said fingers, said fingers being curved and having spaces therebetween and said cap conforming to the curved shape of said fingers for interlockingly snapping thereon, said cap having a slot therein for receiving said portion of dental floss stretched between said branches of said bifurcated portion.

7. The dental floss holder of claim 6 wherein one aspace between said fingers includes a cutting edge attached to a finger for severing dental floss placed within said space when said cap is snapped over said fingers.

8. A dental floss holder comprising, in combination:
   a. an elongate, partially hollow handle adapted to hold a supply of dental floss interior thereto, one end of said handle having a circular aperture defined therein with interior threads;
   b. lock means disposed interior to said handle for fixedly grasping a portion of dental floss; and
   c. a plurality of tips adapted to be removably attached alternatively to said handle, each said tip having a bifurcated portion, a cylindrical, threaded mounting member attached to said bifurcated portion for mating insertion in said end of said handle having said threaded aperture, thereby attaching said tip to said handle, fastener means disposed at the extremity of a first branch of said bifurcated portion for securing a free end of a portion of dental floss grasped by said lock means and stretched tightly between the two branches of said bifurcated portion, and a channel-like passageway formed in said tip and running from the hollow interior of said handle to the extremity of said second branch for threading said dental floss out from the interior of said handle to said extremities of the branches of said bifurcated portion.

9. A dental floss holder comprising, in combination:
 a. an elongate, partially hollow body adapted to hold a supply of dental floss interior thereto;
 b. tip means having a bent portion defining a gap between a first and a second end thereof, said first end being attached to a front end of said body, for holding a tightly stretched length of dental floss between said front end of said body and said second end of said tip;
 c. an elongate shaft disposed interior to said body longitudinally relative thereto;
 d. releasable clasp means disposed interior to said body and coupled to the front end of said shaft for fixedly grasping a portion of dental floss; and e. end means movably coupled to the rear of said body and connected to said shaft for acting through said shaft to cause said clasp means to release its grasp in response to movement of said end means with respect to the rear of said body.

10. The dental floss holder of claim 9 wherein said clasp means comprises a plurality of longitudinally projecting, outwardly biased pinching members attached to the front end of said shaft, a sleeve having an aperture through which said shaft is inserted such that said shaft may move back and forth longitudinally therein, and a spring connected between said shaft and said sleeve to force said shaft rearwardly enough that said pinching members are wedged into said sleeve thereby forcing said pinching members together, said pinching members being collectively larger than said aperture when they are forced together, and further comprising an end piece removably attached to the rear of said body for coupling said end means thereto, said end means comprising a push-button for pushing said shaft forwardly, thereby permitting said pinching members to expand outwardly and release said floss.

11. The dental floss holder of claim 9 wherein said clasp means comprises a pair of substantially parallel plates a first one of which is fixedly mounted to the front end of said elongate shaft and the second one of which is rotatably mounted to the front end of said shaft in front of said first plate, each said plate contacting the inner surface of said body at one point along its edge such that friction at said point of contact tends to resist rotation of said plates about the axis of said shaft and each said plate having a point along its edge being a predetermined distance from the interior surface of said body for threading a portion of dental floss therebetween, said end means comprising a handle attached to the rear end of said shaft and rotatably attached to said body for axially rotating said shaft to turn said first plate.

12. The dental floss holder of claim 11 wherein the interior cross-section of said hollow body is round and said plates are oblong in shape, their greatest width being equal to the interior diameter of said body.

13. The dental floss holder of claim 9 further including a spool adapted to hold dental floss wound thereon rotatably mounted on said shaft.

* * * * *